United States Patent [19]

Schwartz et al.

[11] Patent Number: 5,348,970
[45] Date of Patent: Sep. 20, 1994

[54] ANTIFUNGAL COMPOUND AND COMPOSITIONS CONTAINING THE COMPOUND

[75] Inventors: Robert E. Schwartz, Scotch Plains; Janet C. Onishi, Westfield; Gerald F. Bills, Cranford; Robert A. Giacobbe, Lavallette, all of N.J.; Fernando Pelaez, Madrid, Spain; Maria T. Diez, Madrid, Spain; Francisca Vicente, Madrid; Julian Gorrochategui, Madrid, Spain; Gregory L. Helms, Fanwood; Barnali Pramanik, Somerset, both of N.J.

[73] Assignee: Merck & Co., Inc., Rahway, N.J.

[21] Appl. No.: 125,432

[22] Filed: Sep. 22, 1993

[51] Int. Cl.$^5$ .................... A61K 31/40; C07D 405/06
[52] U.S. Cl. ................................... 514/422; 548/517
[58] Field of Search ......................... 548/517; 514/422

[56] References Cited

U.S. PATENT DOCUMENTS 5,281,717  1/1994  Murata et al. ...................... 548/517

Primary Examiner—Robert W. Ramsuer
Assistant Examiner—Joseph K. McKane
Attorney, Agent, or Firm—Mark Daniel; Elliott Korsen

[57] ABSTRACT

A compound of the formula 1:

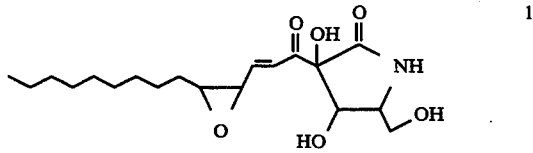

is produced via fermentation of a fungal isolate ATCC no. 74235.

The organism is included herein, as well as a process for production of the compound, a pharmaceutical composition and a method of treatment.

5 Claims, 1 Drawing Sheet

ANTIFUNGAL COMPOUND AND COMPOSITIONS CONTAINING THE COMPOUND

BACKGROUND OF THE INVENTION

The present invention relates to an antifungal agent which was derived from a fungal isolate which was taken from a sample of grass. Presently used antifungal compounds exhibit high levels of toxicity when used systemically at therapeutically effective doses. Others, such as the econazoles, are less toxic but less efficacious. Lastly, the resistance of opportunistic fungal organisms to currently used antifungal agents has been changing, with the incidence of resistance increasing. More resistant organisms are being isolated. Consequently, there is a need for antifungal compounds which have high levels of potency and reduced levels of toxicity when used at therapeutically effective levels.

SUMMARY OF THE INVENTION

An antifungal compound of the formula I:

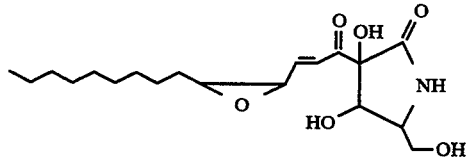

is disclosed. Pharmaceutically acceptable esters and hydrates are included.

Also included is a biologically pure culture of the fungal isolate which is useful for producing a compound of formula 1.

Also included is a process for producing a compound of formula 1 as the major antibiotic product. The fermentation is cultivated using a biologically pure culture of the isolate under aerobic conditions in a nutrient medium containing assimilable sources of carbon, nitrogen and inorganic salts. The cultivation is continued until production of the compound of formula (I) is substantially complete as determined by bioassay or HPLC assay against a pure standard. Thereafter the compound is separated from the medium.

Also included is a pharmaceutical composition which is comprised of the compound of formula 1 in combination with a pharmaceutically acceptable carrier.

Also included is a method of treating fungal or bacterial infection in a mammal in need of such treatment, which is comprised of administering the compound of formula I to the mammal in an amount effective to treat said infection.

BRIEF DESCRIPTION OF THE DRAWINGS

The invention is described below in detail in connection with FIG. I which is an NMR spectrum corresponding to a compound of formula 1.

DETAILED DESCRIPTION OF THE INVENTION

Figure 1:
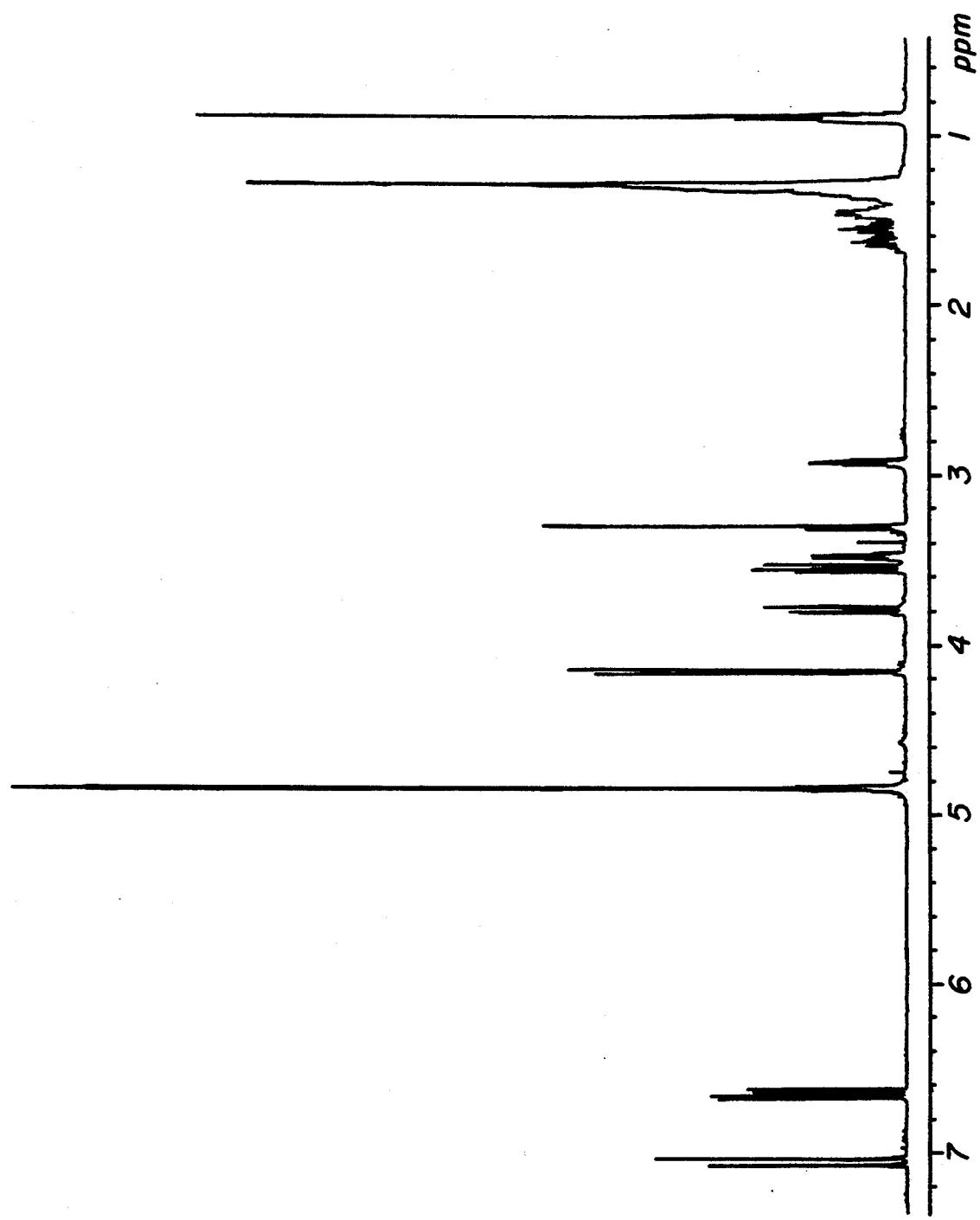

A compound of the formula 1 is described herein in detail, including a method of fermentatively producing the compound using a fungal isolate known as MF 5868 (ATCC No. 74235 deposited Aug. 11, 1993). MF 5868 was made under the Budapest Treaty with the American Type Culture Collection at 12301 Parklawn Drive, Rockville, Md. 20852. The following numbering system is used to describe the compound produced, as well as derivatives thereof:

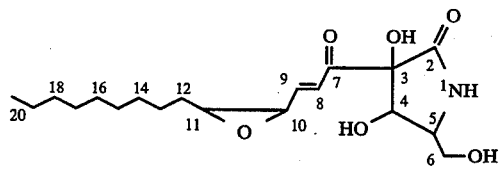

The compound can be produced via a solid or liquid fermentation of the fungal isolate. This fungus was isolated from the internal tissues of surface-sterilized culms of an unidentified grass collected in Sussex County, N.J. The culture was preserved in the Merck Culture Collection (MF 5868) and has been deposited with the American Type Culture Collection (ATCC No. 74235) deposited on Aug. 11, 1993. The organism grows on a variety of mycological media, as further described below, under different light regimes, and on cellulosic materials, such as sterilized leaves and filter paper. The organism has failed to sporulate and thus cannot be identified.

The compound of formula 1 contains seven carbon atoms at which stereoconfiguration can be varied, namely, carbon atoms 3, 4, 5, 8, 9, 10 and 11. All variations of stereoconfiguration are included in the invention, in pure form and in mixture. The NMR spectrum for the compound is shown in FIG. 1.

The most preferred stereoconfiguration for a compound of formula 1 is shown below in FIG. 1A.

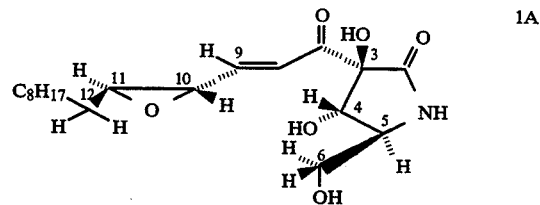

The $^{13}C$ and $^1H$ NMR spectra are set forth below in Table A.

TABLE A

| $^{13}C$ and $^1H$ NMR Assignments for 1 in $CD_3OD$. | | |
|---|---|---|
| Carbon | $^{13}C$ NMR | $^1H$ NMR |
| 7 | 197.88 | C |
| 2 | 174.94 | C |
| 9 | 145.13 | CH | 6.64 dd (15.6, 7.0) |
| 8 | 127.84 | CH | 7.05 dd (15.6, 0.7) |
| 3 | 88.09 | C |
| 4 | 78.90 | CH | 4.15 d (7.2) |
| 11 | 62.88 | CH | 2.93 ddd (6.2, 4.9, 1.9) |
| 6 | 61.99 | $CH_2$ | 3.79 dd (11.7, 2.8) |
|   |       |        | 3.55 dd (11.7, 5.4) |
| 5 | 60.26 | CH | 3.47 ddd (7.2, 5.4, 2.8) |
| 10 | 57.79 | CH | 3.31 ddd (~7 obs, 1.9, 0.7) |
| 12 | 33.05 | $CH_2$ | 1.60 m |
| 14–18 | 33.05 | $CH_2$ | 1.29 bs |
| 14–18 | 30.66 | $CH_2$ | 1.29 bs |
| 14–18 | 30.63 | $CH_2$ | 1.29 bs |
| 14–18 | 30.51 | $CH_2$ | 1.29 bs |
| 14–18 | 30.44 | $CH_2$ | 1.29 bs |
| 13 | 26.97 | $CH_2$ | 1.45 m |
| 19 | 23.73 | $CH_2$ | 1.29 bs |
| 20 | 14.43 | $CH_3$ | 0.89 t (6.8) |

Without limiting the invention to a particular mechanism of action, the compound of formula 1 appears to be fungicidal and bactericidal. It is expected to be less toxic than other fungicidal compounds, e.g., amphotericin B.

Morphology

In agar culture, the fungus exhibits the following morphology: Colonies on oatmeal agar (Difco) at 25° C., 12 hr photoperiod attaining 35 mm in 7 days, slightly raised, with advancing zone oppressed, even, with lanose to floocose, dull, obscurely zonate, at first white but soon pale gull gray, light gull gray, light olive-gray, olive-gray, to gray bluish gray, gull gray, storm gray to dull olivaceous black, dusky green-gray in age developing small hemispherical or pulvinate mycelial masses that resemble protoperithecia or conidiomata, mycelial masses forming droplets of a clear exudate, with surfaces becoming lacunose in age due to collapse or evaporation of exudate droplets with reverse dull gray.

Colonies on Emerson's Yp Ss agar (Difco) at 25° C., 12 hr photoperiod attaining 44–48 mm in 7 days, similar in appearance to colonies on oatmeal agar except margin is more appressed, surface is more zonate, with less development of sterile mycelial masses, reverse dull gray to olivaceous black, zonate.

Colonies on Blakeslee's malt agar at 25° C., 12 hr photoperiod attaining 60–61 mm in 7 days, similar in appearance as above, but less zonate. No growth at 37° C.

Hyphal cells are multinucleate when viewed by flurorescent staining with 4', 6'-diamidino-2-phenyindole (Sneh, B., Burpee, L. & Ogoshi, A. 1991. *Identification of Rhizoctonia species*. American Phytopathological Society: St. Paul). The mycelium is composed of highly branched, simple septate, dematiaceous hyphae characteristic of many ascomycetous fungi.

Fermentation

Fermentation can be conducted in a solid or liquid process, preferably a liquid process, to produce large quantities of a compound of formula 1. The preferred liquid medium is designated LCM (See Table 3 below). LCM may shorten the fermentation time from about 21 days to about 8 days. Also, the yield may be increased about 1.5 fold over solid medium F1.

Extraction of the fermentation medium can be undertaken with a suitable organic phase. The preferred organic phase is comprised of methyl ethyl ketone (MEK).

During the growth of the batch, production of the compound can be monitored by HPLC analysis. When this particular analysis was conducted, e.g., at days 2, 7, 8, 12, 14 and 20, the maximum amount of compound 1 was reached by day 8 (292 mg/L).

The fermentation medium may contain a variety of carbon sources which can be used during the fermentation. The preferred sources of carbon are galactose, glucose, sucrose and fructose. These provided about 2.75 fold increases in production of compound 1 over the original solid medium F1.

More preferably, the carbon source is galactose, such as in LCM-1 (Table 4), or glucose, as in LCM-2, (Table 5).

The temperature range of 16° to 37° C. was determined to provide suitable growth, with 25° C. being most preferred.

EXAMPLE 1

Fermentation conditions for the production of compound 1 by ATCC No. 74235 were as follows:

Vegetative mycelia of the culture were prepared as described in R. Schwartz, et al. *J. Antibiotics* 42: 163 (1989), by inoculating 54 ml of KF seed medium (Table 1) in a 250 ml unbaffled Erlenmeyer flask with 2-ml of mycelia in 10% glycerol (MF5868) that had been stored at −80° C. Seed cultures were incubated for 3 days at 25° C. and 50% relative humidity on a rotary shaker with a 5-cm throw at 220 rpm in a room with constant fluorescent light.

Pelleted growth was blended for 10–20 seconds in a Waring blender prior to use. Two ml portions of the culture were then used to inoculate a second stage seed culture and further incubated for 2 days as stated above. Two ml portions of this 2 day culture were used to inoculate a solid cracked corn based medium F1 (Table 2) or 50 ml portions of liquid production media LCM, LCM-1, and LCM-2 (Tables 3, 4 and 5) or FOF (Table 6) in 250 ml unbaffled Erlenmeyer flasks. The liquid fermentation flasks were shaken at 220 rpm while the solid cracked corn based medium was grown under static conditions. All other incubation parameters remained the same as stated above.

Maximal production of compound 1 occurred in production media LCM-1 and LCM-2 by day 8 (500 mg/L). At harvest, compound 1, was extracted from the culture with 70 mL of MEK per 250 mL Erlenmeyer flask from the liquid media (LCM series and FOF) or with 50 mL per 250 mL Erlenmeyer flask from the solid cracked corn based medium F1 by shaking with the solvent at 220 rpm for 1 hour at 25° C. The samples were centrifuged for 20 min. at 3000 rpm to obtain the MEK layer.

TABLE 1

| KF SEED MEDIUM | |
| --- | --- |
| Component | per liter |
| Corn Seep Liquor | 5 g |
| Tomato Paste | 40 g |
| Oat flour | 10 g |
| Glucose | 10 g |
| Trace Element Mix* | 10 ml | pH = 6.8
*see Table 1A below

TABLE 1A

| TRACE ELEMENT MIX | |
| --- | --- |
| Component | per liter |
| $FeSO_4.7H_2O$ | 1 g |
| $MnSO_4.4H_2O$ | 1 g |
| $CuCl_2.2H_2O$ | 25 mg |
| $CaCl_2$ | 100 mg |
| $H_3BO_3$ | 56 mg |
| $(NH_4)_6Mo_7O_{24}.4H_2O$ | 19 mg |
| $ZnSO_4.7H_2O$ | 200 mg |

TABLE 2

| PRODUCTION MEDIUM F1 | |
| --- | --- |
| Component | Amount (per 250 ml flask) |
| Cracked Corn (Bay-mor) | 10 g |
| Ardamine PH (Champlain Industries Inc.) | 2.0 mg |
| $KH_2PO_4$ | 1.0 mg |
| $MgSO_4.7H_2O$ | 1.0 mg |
| Na tartrate | 1.0 mg |
| $FeSO_4.7H_2O$ | 0.1 mg |
| $ZnSO_4.7H_2O$ | 0.1 mg |
| Distilled Water | 10 ml |

TABLE 3

| PRODUCTION MEDIUM LCM | |
| --- | --- |
| Component | per liter |
| Lactose | 75 g |
| Corn Meal (Quaker Oats Co.) | 20 g |
| Ardamine PH | 5 g |
| L-Leucine | 3.5 g |
| MES* | 16.2 g |

*MES = 2-(N-morpholino)-ethanesulfonic acid
Note: pH adjusted to 6.0 with NaOH before autoclaving.

TABLE 4

| PRODUCTION MEDIUM LCM-1 | |
| --- | --- |
| Component | per liter |
| Galactose | 75 g |
| Corn Meal | 20 g |
| Ardamine PH | 5 g |
| L-Leucine | 3.5 g |
| MES* | 16.2 g |

*2-(N-morpholino)-ethanesulfonic acid
Note: pH adjusted to 6.0 with NaOH before autoclaving.

TABLE 5

| PRODUCTION MEDIUM LCM-2 | |
| --- | --- |
| Component | per liter |
| Glucose | 75 g |
| Corn Meal | 20 g |
| Ardamine PH | 5 g |
| L-Leucine | 3.5 g |
| MES* | 16.2 g |

*2-(N-morpholino)-ethanesulfonic acid
Note: pH adjusted to 6.0 with NaOH before autoclaving

TABLE 6

| PRODUCTION MEDIUM FOF | |
| --- | --- |
| Component | per liter |
| Fructose | 75 g |
| Oat Flour | 15 g |
| Fidco Yeast Extract | 5 g |
| L-Glutamic Acid | 4 g |
| MES* | 16.2 g |

*2-(N-morpholino)ethanesulfonic acid
Note: pH adjusted to 6.0 with NaOH before autoclaving

EXAMPLE 2

Isolation of Compound (1)

After 21 days of growth in a solid cracked corn-based medium, as described above, the contents of 18 flasks were mixed with 50-ml portions of methyl ethyl ketone (MEK) and shaken at 220 rpm for 1 hour at 25° C. The titer of (1) via HPLC was 200 mg/L. The mixture was filtered and the resulting 700 ml of filtrate was diluted to 900 ml with additional MEK. Six hundred and fifty ml of hexane was added to 650 ml of this MEK extract, which resulted in a 65 ml lower. aqueous-rich layer and an 1120 ml MEK/hexane upper layer, which contained 1. The upper layer was concentrated to dryness in vacuo and partitioned between 65 ml MeOH and 65 ml hexane. This yielded an upper hexane layer of 24 ml and a lower MeOH/hexane layer of 118 ml, which contained compound 1.

The lower layer from the second partition was concentrated to dryness, reconstituted in 10 ml EtOAc, and chromatographed on 460 ml silica gel 60 (EM Science, 230–400 mesh) column using a step gradient (EtOAc, EtOAc/MeOH 98:2, EtOAc/MeOH 90:10, EtOAc/MeOH 50:50). The compound of interest was located in the composite rich cut eluting with EtOAc/MeOH 90:10.

The silica gel rich cut was concentrated to dryness, reconstituted in 2 ml of MeOH/$H_2O$ (95:5), centrifuged, and a 0.5 ml portion chromatographed on a 2.12×25 cm Zorbax RX C-8 column using MeOH/$H_2O$ 70:30. A 12.6 mg sample ($1_{max}$ MeOH 245, E% 391) of 1 was obtained upon lyophilization of the rich cut from preparative HPLC.

Compound 1 was crystallized from methanol/water (m.p. 110°–113° C.) UV $\lambda_{max}$ 245 nm ($\epsilon$ 14,428). IR 3000–3600, 1708, 1688 $cm^{-1}$.

Five additional components were isolated and/or synthesized. These compounds were determined to have only marginal antifungal and gram positive antibacterial activity when tested in vitro.

The compound of the invention was determined to have antifungal and antibacterial activity.

Minimum Inhibitory Concentrations The antifungal activity of the compound of formula 1 was determined using broth dilution assays. The compound was dissolved in DMSO at 3.7 mg/mL and serially diluted in 1% aqueous DMSO. The yeast strains including Candida species and Cryptococcal species were grown to exponential phase in a complex medium composed of 1% peptone, 0.5% yeast extract and 0.05% dextrose (CM) at 29° C. The yeast cells were diluted in CM to $A_{600}$=0.004 U/mL which was previously determined to be equal to 3000 colony forming units per milliliter. 180 uL of inoculated CM was added to the wells of a 96 well microtiter dish containing 20 $\mu$L of diluted inhibitor samples. The final concentration of the compound in the wells ranged from 37–0.01 $\mu$g/ml. The microtiter dishes were incubated for 18 hours at 29° C. and visually inspected for growth. The minimum inhibitory concentration (MIC) was recorded as the lowest concentration of compound to prevent visible growth.

The same procedure was used to determine the MIC of the compound against the filamentous fungi, Aspergillus fumigatus MF 5668, except a spore inoculum was prepared. Spores of A. fumigatus were obtained by washing a well sporulated slant of the organism growing on potato dextrose agar with 0.05% tween 80 solution. The spore solution was diluted in CM to an $A_{600}$=0.04 U/mL which was previously shown to equal 3000 colony forming units per milliliter. The spore solution was diluted in CM to an $A_{600}$=0.04 U/mL which was previously shown to equal 3000 colony forming units per milliliter.

| Antifungal activity of Compound 1 | | |
| --- | --- | --- |
| Organism | Merck Culture Number | MIC Compound 1 $\mu$g/mL |
| Candida albicans | MY 1055 | 7.4 |
| Candida parapsilosis | MY 1010 | 1.5 |
| Candida tropicalis | MY 2167 | 7.4 |
| Candida krusei | MY 2168 | >37.0 |
| Cryptococcus neoformans | MY 2061 | 7.4 |
| Cryptococcus neoformans | MY 2062 | 0.02 |
| Aspergillus fumigatus | MF 5668 | 37.0 |

The antibacterial activity of the compound was determined using broth dilution assays. The compound was dissolved in DMSO at 10 mg/mL and serially diluted in Luria Broth (LB), composed of 10% tryptone, 5% yeast extract and 5% sodium chloride. The Enterococcal strains were grown in Brain Heart Infusion broth; *Staphylococcus aureus* (MB2865) was grown in LB; *S. aureus* (MB108) and (MB2949) and *Proteus vulgaris* were grown in Nutrient Broth with 2% yeast extract. All bacterial strains were incubated overnight at 37° C. The bacterial cells were diluted $10^{-4}$ in LB to give approximately $5 \times 10^4$ to $1 \times 10^5$ colony forming units per milliliter. 180 μL of inoculated LB was added to the wells of a 96 well microtiter dish containing 20 μL of diluted inhibitor samples. The final concentration of the compound in the wells ranged from 500–0.00025 μg/ml. The microtiter dishes were incubated for 24 hours at 28° C. and visually inspected for growth. The minimum inhibitory concentration (MIC) was recorded as the lowest concentration of compound to prevent visible growth.

| Antibacterial activity of Compound 1 | | |
|---|---|---|
| Organism | Merck Culture Number | MIC (μg/ml) |
| Staphlococcus aureus | MB 2865 | 0.5 |
|  | MB 108 | 0.5 |
|  | MB 2949 | 125–250 |
| *Entercoccus faecium* | MB 5571 | 2.0 |
|  | MB 5572 | 1.0 |
| *Proteus vulgaris* | MB 838 | >500 |

In vitro activity determined in accordance with the protocols set forth herein is often predictive of in vivo utility, when the compound is administered to a mammal infected with a susceptible organism.

Minimum inhibitory concentrations for different compounds may also be calculated using the procedures set forth in Lorian, V. (ed.) *Antibiotics in Laboratory Medicine* (3rd ed.) pages 30–35 if desired. By comparing disc sensitivities to a known compound, e.g., amphotericin B or pneumocandin, this calculation is not required to recognize antifungal activity.

The compound of the present invention may thus become a valuable antifungal/antibacterial agent which can be used in human and veterinary medicine. The compound is not limited to utility as a medicament; it may be used in other ways, for example, such as an additive to animal feed, as a preservative or antifungal sterilizing agent for food preparation, as a disinfectant and in other industrial systems where control of fungal growth is desired. For example, it may be employed in concentrations ranging from about 0.01 to about 100 parts per million to destroy or inhibit the growth of fungal organisms in water based paints and in the white water of paper mills to inhibit the growth of harmful bacteria.

The compounds of the present invention are useful per se and in the form of pharmaceutically acceptable esters, hydrates or hemihydrates. The term "pharmaceutically acceptable esters, hydrates or hemihydrates," refers to those esters and hydrated forms of the compound which would be apparent to the pharmaceutical chemist. i.e., those which are substantially non-toxic and which may favorably affect the pharmacokinetic properties of the compound, their palatability, absorption, distribution, metabolism and excretion.

Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredient in combination with pharmaceutically acceptable carriers. Thus, the present invention is also concerned with pharmaceutical compositions and methods of treating fungal infections utilizing as an active ingredient the novel compound.

The pharmaceutically acceptable esters of the present invention are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947.

The esters which are hydrolizable under physiological conditions may also be referred to as "biolabile esters". Many biolabile esters have oral activity, protecting the drug from excessive acid degradation upon oral administration. Biolabile esters are biologically hydrolizable, and many are suitable for oral administration, due to good absorption through the stomach or intestinal mucosa, resistance to gastric acid degradation and other factors. Examples of biolabile esters include compounds in which the esterifying group contains an alkoxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. All of these groups can be substituted in the alkyl or aryl portions thereof with acyl or halo groups. The following species are preferred as biolabile ester forming moieties.: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

Some of the compounds of the present invention may also be in association with a readily removable protecting group, such as for the hydroxyl groups at positions 3, 4 and 6. Such conventional groups consist of known groups which are used to protectively block the hydroxyl groups during the chemical synthesis of the compound. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation. Examples of such protecting groups include benzhydryl, p-nitrobenzyl, 2-naphthylmethyl, allyl, benzyl, trichloroethyl, silyl such as trimethylsilyl or trimethylsilylethyl, phenacyl, p-methoxybenzyl, acetonyl, o-nitrobenzyl, p-methoxyphenyl, 4-pyridylmethyl, and t-butyl.

The compound of this invention may be used in a variety of pharmaceutical preparations. They may be employed in powder or crystalline form, in liquid solution or in suspension. They may be administered by a variety of means; e.g., topically, orally and parenterally by injection (intravenously or intramuscularly).

Compositions for injection, a preferred route of delivery for serious infections, may be prepared in unit dosage form in ampoules, or in multidose containers. The injectable compositions may take such forms as suspensions, solutions, or emulsions in oily or aqueous vehicles, and may contain formulating agents. Alternatively, the active ingredient may be in powder (lyophillized or non-lyophillized) form for reconstitution at the time of delivery with a suitable vehicle, such as sterile water.

Topical applications may be formulated in hydrophobic or hydrophilic bases as ointments, creams, lotions, paints, powders, aerosol sprays and the like. The preferred compositions for superficial fungal infections are topical creams, ointments, solutions and sprays.

Oral compositions may take such forms as tablets, capsules, oral suspensions and oral solutions. The oral compositions may utilize conventional formulating agents, and may include sustained release properties as well as rapid delivery forms.

The compositions for human delivery per unit dosage, whether liquid or solid, may comprise from about 0.01% to as high as about 99% active material, the preferred range being from about 10 to about 60%. The composition will generally contain from about 1 mg to about 2.5 g of the active ingredient; however, in general, it is preferable to employ a dosage amount in the range of from about 25 mg to 1000 mg. In topical applications, the size of the dose applied or administered will typically be a function of the area to be treated, whereas with respect to parenteral administration, the predetermined unit dosage will typically include the pure compound in sterile water solution or in the form of a soluble powder intended for solution, which can be adjusted to neutral pH and isotonic.

The invention described herein encompasses a method of treating a fungal infection in a mammal in need of such treatment. The mammal is administered a compound of the invention in an amount which is effective to treat the fungal infection. The dosage to be administered depends to a large extent upon the condition and size of the subject being treated, the route and frequency of administration, the sensitivity of the pathogen to the compound selected, the virulence of the infection and other factors. Such matters, however, are left to the routine discretion of the physician according to principles of treatment well known in the art. Another factor influencing the precise dosage regimen, apart from the nature of the infection and peculiar identity of the individual being treated, is the molecular weight of the compound.

The preferred methods of administration of the Formula I antifungal compounds include topical, oral and parenteral, e.g., i.v. infusion, i.v. bolus and i.m. injection.

For superficial infections, such as the condition known as "athlete's foot", the dosage for adults and children is generally the same, depending upon the area to be treated. The compound is typically applied to the affected area in the form of a cream, ointment, spray or solution from one to four times daily, in an amount sufficient to treat the effected area.

For systemic use in adults, about 5-50 mg of the compound per kg of body weight may be given one to four times daily. The preferred dosage is 25 mg to 1000 mg of the compound given one to four times per day. More specifically, for mild infections a dose of about 25 mg two or three times daily may be recommended. For moderate infections against highly susceptible gram positive organisms a dose of about 500 mg three or four times a day may be required. For severe, life-threatening infections against organisms at the upper limits of sensitivity to the compound, a dose of about 1000-2000 mg three to four times daily may be necessary.

For children, a dose of about 0.5-25 mg/kg of body weight given 2, 3, or 4 times per day is preferred; a dose of about 1.0 mg/kg is typically recommended, and adjusted based upon the patient's response.

The preferred embodiments of the invention have been described herein in detail. However, numerous alternative embodiments are contemplated as falling within the scope of the invention. Consequently, the scope of the claims is not to be limited to the specific teachings contained herein.

What is claimed is:

1. A compound represented by formula I:

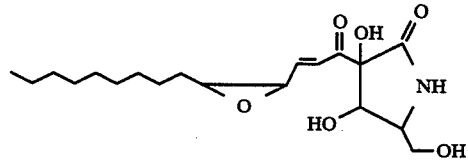

or a pharmaceutically acceptable ester or hydrate thereof.

2. A compound in accordance with claim 1, having the structure:

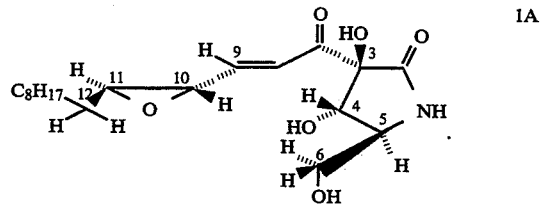

3. A pharmaceutical composition comprised of a compound in accordance with claim 1 in combination with a pharmaceutically acceptable carrier.

4. A method of treating a fungal infection in a mammal in need of such treatment comprising administering to said mammal a compound in accordance with claim 1 in an amount effective to treat said fungal infection.

5. A method of treating a bacterial infection in a mammal in need of such treatment comprising administering to said mammal a compound in accordance with claim 1 in an amount effective to treat said bacterial infection.

* * * * *